Figure 1B:
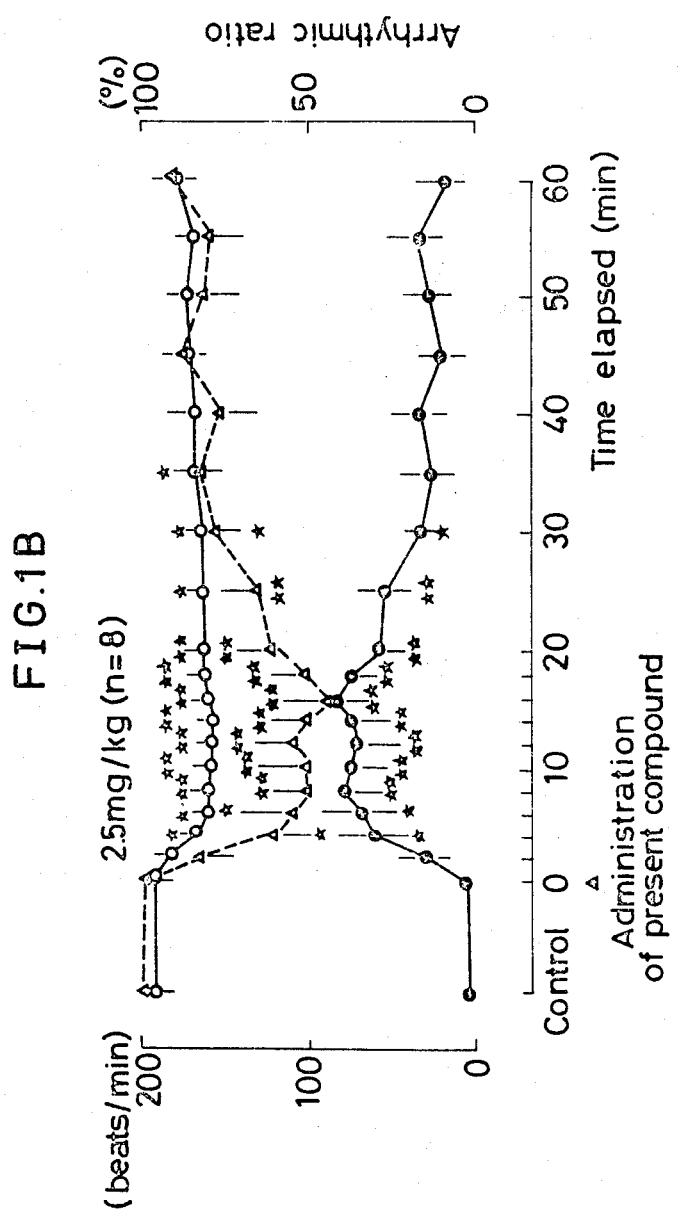

United States Patent

Satoh et al.

[11] Patent Number: 4,751,232
[45] Date of Patent: Jun. 14, 1988

[54] PYRROLIZIDINE DERIVATIVE AND PHARMACEUTICAL COMPOSITION THEREOF

[75] Inventors: Fumio Satoh, Nagaokakyo; Keiyu Shima, Kyoto; Takafumi Ishihara, Toyonaka, all of Japan

[73] Assignee: Suntory Limited, Osaka, Japan

[21] Appl. No.: 703,913

[22] Filed: Feb. 21, 1985

[30] Foreign Application Priority Data

Feb. 29, 1984 [JP] Japan ................... 59-39199

[51] Int. Cl.⁴ .................... A61K 31/40; C07D 487/06
[52] U.S. Cl. ................................... 514/413; 548/453
[58] Field of Search ...................... 548/453; 514/413

[56] References Cited

U.S. PATENT DOCUMENTS

| | | | |
|---|---|---|---|
| 4,213,983 | 7/1980 | Hadley et al. | 514/413 X |
| 4,564,624 | 1/1986 | Miyano et al. | 514/413 |

FOREIGN PATENT DOCUMENTS

| | | | |
|---|---|---|---|
| 0039903 | 11/1981 | European Pat. Off. | 548/453 |
| 0089061 | 9/1983 | European Pat. Off. | 548/453 |
| 0095345 | 11/1983 | European Pat. Off. | 453/ |

Primary Examiner—Glennon H. Hollrah
Assistant Examiner—D. B. Springer

Attorney, Agent, or Firm—Burgess, Ryan & Wayne

[57] ABSTRACT

A novel pyrrolizidine derivative of the formula,

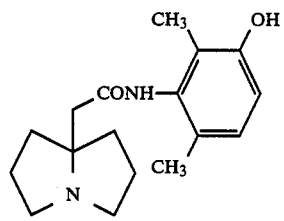

which has potent antiarrhythmic activity and low toxicity is produced.

The derivative can be synthesized: by acylating 2,6-xylidine to protect the amino group, nitrating the protected xylidine to introduce a nitro group at 3-position, reducing the nitro group to an amino group, followed by diazotizing and hydrolyzing, and then the resulted 3-hydroxy-2,6-dimethylaniline being condensed with 8-halocarbonylmethylpyrrolizidine; or by nitrating N-(2',6'-dimethyl)phenyl-8-pyrrolizidineacetamide to introduce a nitro group at 3'-position, reducing the nitro group to amino group, diazotizing the amino group and hydrolyzing the diazonium compound.

2 Claims, 3 Drawing Sheets

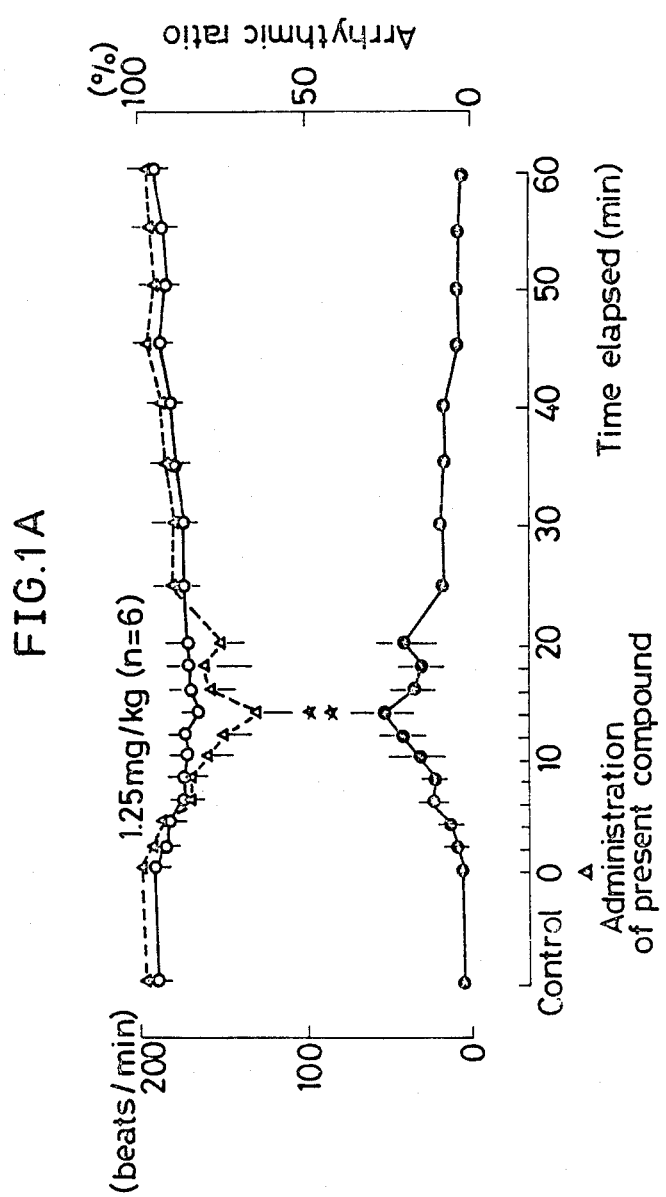

PYRROLIZIDINE DERIVATIVE AND PHARMACEUTICAL COMPOSITION THEREOF

The present invention relates to a novel pyrrolizidine derivative. As described in European Patent Application Publication NO. 0 089 061, certain 8-substituted derivatives have potent antiarrhythmic activity. As a result of their further investigations, the present inventors found that the pyrrolizidine derivative of the formula (I) has potent antiarrhythmic activity and they have now completed the present invention.

The present invention is directed to a novel pyrrolizidine derivative having the formula given below, i.e. N-(3'-hydroxy-2',6'-dimethyl)phenyl-8-pyrrolizidineacetamide, and a pharmaceutically acceptable salt thereof and to an antiarrhythmic agent containing the same.

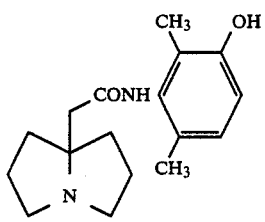

The compound of formula (I) can be produced by the following Method A or B:

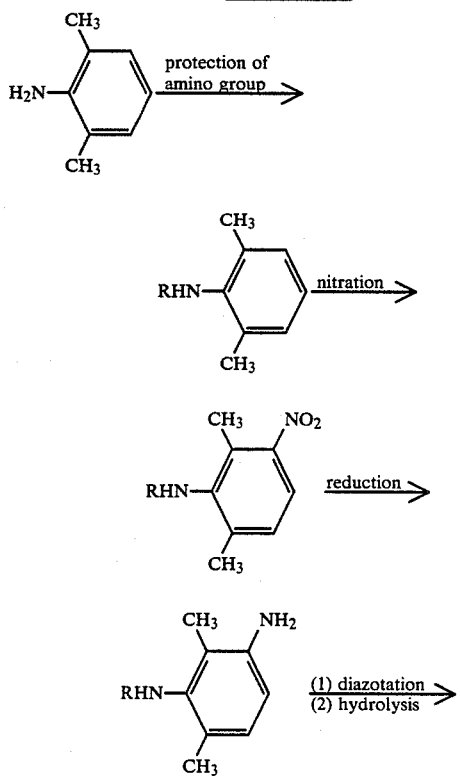

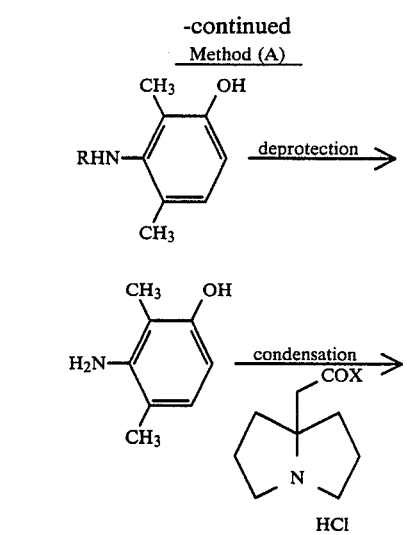

(R is an aryl group and X is a halogen.)

Thus, the amino group of 2,6-xylidine, which is commercially available, is protected with an acyl group such as acetyl or benzoyl and the protected xylidene is reacted with, for example, a mixed acid composed of fuming nitric acid and concentrated sulfuric acid under mild conditions of 0°–10° C. to thereby introduce a nitro group at the desired position. Subsequently, the nitro group is converted into an amino group by catalytic reduction or any other appropriate method and the resultant amine compound is diazotized with a nitrite. The thus-produced diazonium salt is hydrolyzed to the corresponding phenolic compound, which is then condensed with pyrrolidizine substituted at the 8-position with a halocarbonylmethyl group such as chlorocarbonylmethyl, bromocarbonylmethyl etc. as obtained by the method described in European Patent Application Publication No. 0 089 061 to give the desired compound, N-(3'-hydroxy-2',6'-dimethylphenyl)-8-pyrrolizidineacetamide (I).

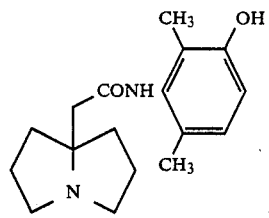

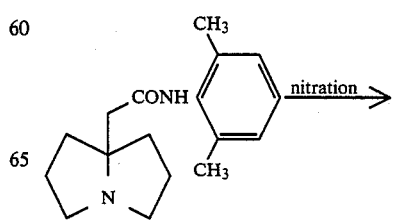

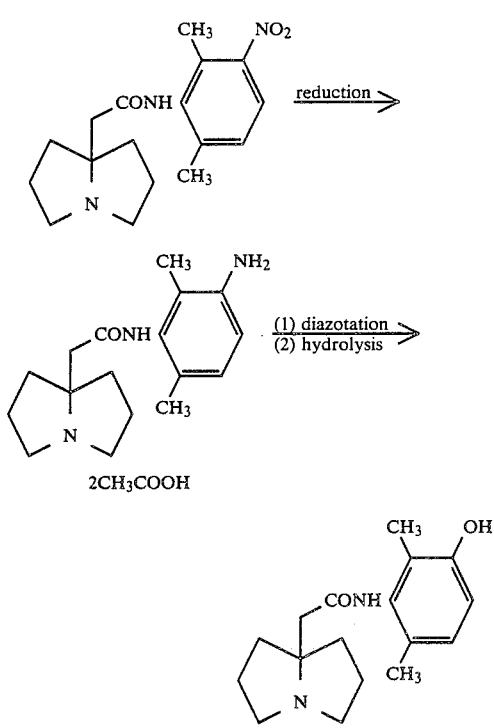

N-(2',6'-Dimethylphenyl)-8-pyrrolizidineacetamide, the compound No. 12 described in Japanese Kokai Tokkyo Koho JP No. 58-159493, is reacted with, for example, a mixed acid composed of fuming nitric acid and concentrated sulfuric acid under mild conditions of 0°–10° C. to thereby introduce a nitro group at the desired position. Subsequently, the nitro group is converted into an amino group by catalytic reduction or any other appropriate method and the resultant amine compound is diazotized with a nitrite. The thus-produced diazonium salt is hydrolyzed to give the desired compound, N-(3'-hydroxy-2',6'-dimethylphenyl)-8-pyrrolizidine (I). N-(3'-Hydroxy-2',6'-dimethylphenyl)-8-pyrrolizidine thus obtained is a novel compound and has antiarrhythmic activity as will be mentioned below.

The term "pharmaceutically acceptable salt" as used herein includes acid addition salts which can be used as drugs, for example, salts with mineral acids such as hydrochloric acid, hydrobromic acid, hydriodic acid and phosphoric acid, and salts with organic carboxylic or sulfonic acids such as trifluoroacetic acid, p-toluenesulfonic acid, maleic acid, acetic acid, citric acid, oxalic acid, succinic acid, benzoic acid, tartaric acid, fumaric acid, mandelic acid, ascorbic acid and malic acid.

Antiarrhythmic activity

According to the method of Langendorff (Circulation 1: 1318, 1950), adult mongrel dogs of either sex, weighing 7 to 12 kg, were used. Under pentobarbital (30 mg/kg, i.v.) anesthesia, the left anterior descending coronary artery of the heart, which was exposed by percardiectomy after the chest was opened through the 5th intercostal space, was dissected free from the surrounding tissues at a site just distal to the first diagonal branch and and two silk threads were passed beneath the dissected artery. At first, the dissected artery was ligated with a thread together with a ¼ gauge needle, and immediately thereafter the needle was withdrawn, leaving the artery constricted partially. Next, the other ligature was tightened completely 30 min later. Twenty-four hours after completion of the coronary artery ligation, limb lead II electrocardiogram (ECG) was recored in order to know if ventricular arrhythmias developed. By intravenous administration of a substance having antiarrhythmic activity at that point, decrease in the number of arrhythmias is observed. The compound of the present invention was intravenously administered to groups of 6 to 8 dogs at doses of 1.25, 2.5 and 5 mg/kg and the animals were observed for 60 minutes after administration. It was found that the compound of the present invention exterted a dose-dependent antiarrhythmic action, as indicated by a decrease in arrhythmic ratio and an increase in the rate of heart beats conducted from the sinoatrial node. The duration of action was also dose-dependent and at 5 mg/kg, the action persisted for more than 1 hour. The total heart rate (○—○), conducted beats (●—●) and arrhythmic ratio (△—△) were estimated, and the estimated values, which were tested for significance of difference from the pretreatment values, are shown in FIG. 1.

Figure 1C:
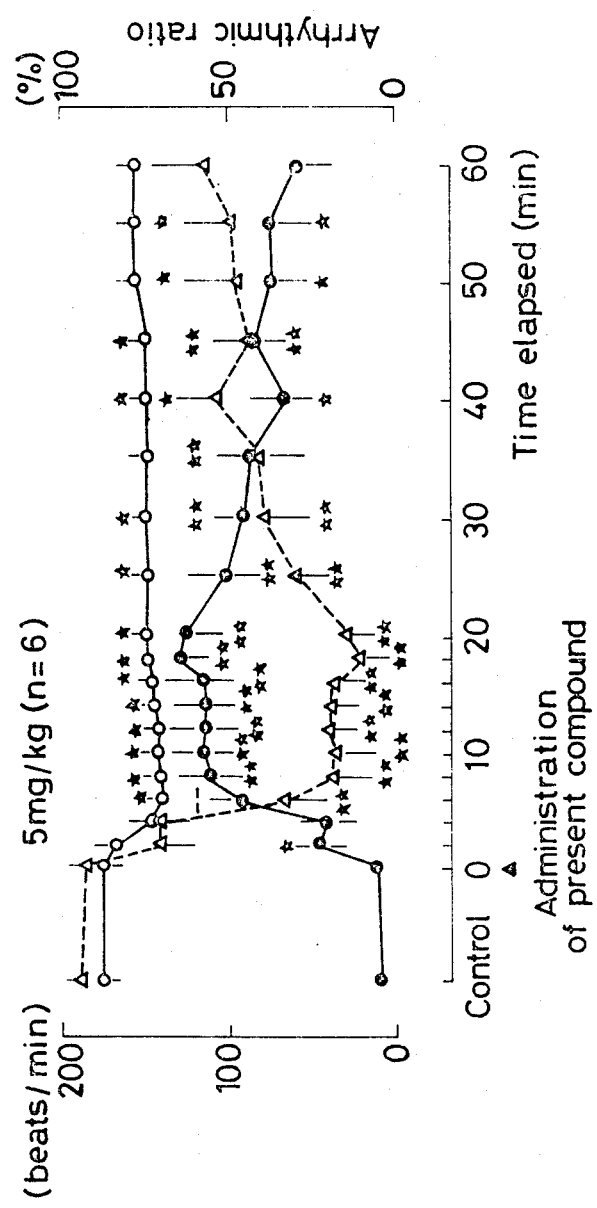

FIGS. 1-A, B and C show the time-course changes in the total heart rate (○), conducted beats (●) and arrhythmic ratio (△) in dogs with ventricular arrhythmia induced by the coronary artery ligation, after intravenous doses of 1.25, 2.5 and 5 mg/kg of the compound of the present invention, respectively.

Acute Toxicity

The $LD_{50}$ values were calculated by the up and down method (Pharmacological Experiments, edited by Takagi and Ozawa, p. 204, Nanzando, 1972) using male ddy mice weighing 12 to 22 g. The intravenous $LD_{50}$ value of the compound of the present invention was found to be 17 mg/kg and the oral $LD_{50}$ value, 375 mg/kg.

For the treatment of arrhythmia, the compound of the present invention or a pharmaceutically acceptable salt thereof can be orally or parenterally administered in the form of appropriate pharmaceutical preparations such as capsule, tablet, injection, etc., alone or in admixture with known non-toxic excipients. Such preparations can be prepared, for example, as follows: the bulk substance is finely divided, admixed with an excipient such as lactose, starch or derivative thereof, or cellulose derivative and packed into gelatin capsules. In manufacturing tablet preparations, the bulk substance is kneaded with binding agents, such as sodium carboxymethylcellulose, alginic acid and gum arabic, and water, together with the above-mentioned excipients. The mixture obtained is granulated using an extruding granulator. The granules are admixed with lubricants such as talc and stearic acid and made into tablets using a conventional tablet-compression machine. For parenteral administration by injection, a water-soluble salt of the compound is dissolved in sterile distilled water or sterile physiological saline and the solution is sealed into ampules for giving injections. If necessary, stabilizers and/or buffers may be added.

While the effective dose of an antiarrhythmic agent varies with the mode of administration, type and severity of arrhythmia and physical conditions of the patient, such agent is generally administered in an amount sufficient to turn abnormal rhythms into normal sinus rhythms. In adult humans, the compound of the present invention is generally administered at a dose of 50–200 mg, 3 or 4 times a day by oral administration or at a dose of 0.5–5 mg/kg by intravenous drip infusion.

EXAMPLE 1

(Method A)

Preparation of N-acetyl-2,6-xylidine

To 25 ml of 2,6-xylidine (0.20 mole) was added slowly a mixture of 25 ml of acetic anhydride (0.26 mole) and 25 ml of acetic acid (0.44 mole) under stirring at room temperature. The mixture was stirred for 30 minutes at room temperature and, then, diluted with water. The crystalline precipitate was collected by filtration to give 30.1 g (91%) of the title compound (m.p. 182°–184° C.; colorless needles).

Preparation of N-acetyl-2,6-dimethyl-3-nitroaniline

To a mixture of 30.1 g of N-acetyl-2,6-xylidine (0.18 mole) and 40 ml of acetic acid (0.70 mole) was added gradually 80 ml of concentrated sulfuric acid (0.50 mole) with stirring under ice-cooling. Then, to the mixture was added slowly 10 ml of fuming nitric acid (0.24 mole) in a manner such that the temperature of the reaction mixture did not exceed 10° C. The reaction mixture was returned to room temperature and, after stirring for 2 hours, poured onto ice. The resulting crystalline precipitate was collected by filtration and recrystallized from ethanol to give 35.5 g (92%) of the title compound (m.p. 171°–173° C.; pale yellow needles).

$IR_{(cm-1}{}^{KBr})$: 1650 (—CONH—) 1520, 1350 (—NO$_2$).
CHCl$_3$+CD$_3$OD
NMR($\delta$, ppm): 2.17(3H, S, —CH$_3$), 2.23(3H, S, —CH$_3$), 2.32(3H, S, —CH$_3$), 7.13(1H, d, J=8 Hz, aromatic proton), 7.66(1H, d, J=8 Hz, aromatic proton).

Preparation of 1-acetamido-3-amino-2,6-dimethylbenzene

N-Acetyl-2,6-dimethyl-3-nitroaniline (30.6 g; 0.15 mole) was dissolved in a mixture of methanol (100 ml), ethanol (50 ml) and acetic acid (100 ml). To the resulting solution was added 2.0 g of 10% palladium carbon and the mixture was stirred in a stream of hydrogen at room temperature for 26 hours. The catalyst was filtered off, the filtrate was concentrated under reduced pressure, and the residue was recrystallized from ethanol-ether to give 22.0 g (84%) of the title object compound as crystals, m.p. 195°–197° C.

$IR_{(cm-1}{}^{KBr})$: 3440, 3350 (—NH$_2$), 1640 (—CONH).
CHCl$_3$+CD$_3$OD
NMR($\delta$, ppm): 1.98(3H, S, —CH$_3$), 2.08(3H, S, —CH$_3$), 2.13(3H, S, —CH$_3$), 6.57(1H, d, J=8 Hz, aromatic proton), 6.83(1H, d, J=8 Hz, aromatic proton)

Preparation of 3-acetamido-2,4-dimethylphenol

1-Acetamido-3-amino-2,6-dimethylbenzene (4.77 g; 26.8 mmol) was dissolved in a diluted acid prepared from concentrated sulfuric acid (3 ml) and water (30 ml). To the resulting solution was added dropwise a solution of sodium nitrite (2.40 g; 34.8 mmol) in water (5 ml) in a manner such that the temperature of the reaction mixture did not exceed 10° C. Then, the mixture was stirred under ice-cooling for 15 minutes. After addition of 1.00 g of urea (16.6 mmol), the mixture was dropwise added gradually into 75 ml of boiling water and the whole mixture was refluxed for 30 minutes. After cooling, sodium chloride was added, followed by extraction with ether and chloroform. The organic layer was washed with water and dried over magnesium sulfate (dehydration), and the solvent was distilled off to give 3.2 g (67%) of the title compound as colorless needles, m.p. 190°–195° C.

$IR_{(cm-1}{}^{KBr})$: 3440–3200 (phenolic OH involved in hydrogen bond), 1650 (—CONH).
CHCl$_3$+CD$_3$OD
NMR($\delta$, ppm): 1.93(3H, S, —CH$_3$), 2.07(3H, S, —CH$_3$), 2.12(3H, S, —CH$_3$), 6.37(1H, d, J=8 Hz, aromatic proton), 6.67(1H, d, J=8 Hz, aromatic proton).

Preparation of 3-amino-2,4-dimethylphenol

A mixture of 10 g of 3-acetamido-2,4-dimethylphenol (55.9 mmol), 250 ml of concentrated sulfuric acid and 200 ml of ethanol was refluxed for 30 minutes and, then, concentrated under reduced pressure. The residue was dissolved in water and the solution was made alkaline with ammonia water and extracted with ether. The ether layer was washed with a saturated aqueous solution of sodium chloride, dried over magnesium sulfate (dehydration) and concentrated under reduced pressure. The residue was recrystallized from ethanolhexane to give 5.3 g (69%) of the title compound as colorless plates, m.p. 177°–179° C.

Preparation of N-(3'-hydroxy-2',6'-dimethylphenyl)-8-pyrrolizidineacetamide hydrochloride 3-Amino-2,4-dimethylphenol (1.4 g; 10.2 mmol) was dissolved in 50 ml of 1,4-dioxane and, under stirring, a solution of 8-chlorocarbonylmethylpyrrolizidine [prepared using 2.10 g of 8-pyrrolizidineacetic acid hydrochloride (10.2 mmol) and 1.5 g of oxalyl chloride (11.8 mmol)] in chloroform (50 ml) was added dropwise thereto. The resulting crystalline precipitate was collected by filtration and, after purification by silica gel column chromatography, recrystallized from ethanol-ether to give 810 mg (25%) of the compound of the present invention as colorless needles, m.p. 280°–283° C. (decomposition).

$IR_{(cm-1}{}^{KBr})$: 1640 (—CONH).
CHCl$_3$+CD$_3$OD
NMR($\delta$, ppm): 3.03(2H, S, —CH$_2$CONH—), 3.33 (6H, S, —CH$_3$ x 2), 6.70 (1H, d, J=8 Hz, aromatic proton), 6.92 (1H, d, J=8 Hz, aromatic proton).

Elemental analysis (% for C$_{17}$H$_{25}$ClN$_2$O$_2$): Calcd: C, 62.85; H, 7.76; N, 8.62. Found: C, 62.75; H, 7.67; N, 8.68.

EXAMPLE 2

(Method B)

Preparation of N-(2',6'-dimethyl-3'-nitrophenyl)-8-pyrrolizidineacetamide

To a mixture of 45.5 g of N-(2',6'-dimethylphenyl)-8-pyrrolizidineacetamide (0.16 mole) and 35 ml of acetic acid (0.61 mole) was added slowly 70 ml of concentrated sulfuric acid with stirring under ice-cooling. The mixture was returned to room temperature for complete dissolution. After cooling again, 9 ml of fuming nitric acid (0.21 mole) was added gradually in a manner such that the temperature of the reaction mixture did not exceed 10° C. The reaction mixture was returned to room temperature and, after stirring for 45 minutes, poured onto ice, and, then, neutralized with potassium carbonate. Subsequently, the solution was made alkaline with 40% sodium hydroxide and extrated with chloroform. The chloroform layer was washed with a saturated aqueous solution of sodium chloride, dried over magnesium sulfate (dehydration) and concentrated under reduced pressure to give 47.9 g (90%) of the title compound.

CDCl₃
NMR(δ, ppm): 2.30 (3H, S, —CH₃), 2.37 (3H, S, —CH₃), 2.53 (2H, S, —CH₂CONH—), 7.10 (1H, d, J=8 Hz, aromatic proton), 7.57 (1H, d, J=8 Hz, aromatic proton).

Preparation of
N-(3'-amino-2',6'-dimethylphenyl)-8-pyrrolizidineacetamide diacetate N-(2',6'-Dimethyl-3'-nitrophenyl)-8-pyrrolizidineacetamide (47.9 g) (0.15 mole) was dissolved in a mixture of 200 ml of ethanol and 30 ml of acetic acid (0.52 mole) and, then, 2.0 g of 10% palladium-carbon was added. The mixture was stirred at room temperature for 204 hours while passing a hydrogen gas therethrough. The catalyst was filtered off and the filtrate was concentrated under reduced pressure to give 57.8 g (94%) of the title compound as an oily substance.

Preparation of
N-(3'-hydroxy-2',6'-dimethylphenyl)-8-pyrrolizidineacetamide hydrochloride N-(3'-Amino-2',6'-dimethylphenyl)-8-pyrrolizidineacetamide diacetate (42.8 g; 0.105 mole) was dissolved in a diluted acid composed of 16 ml of concentrated sulfuric acid and 120 ml of water and, then, a solution of sodium nitrite (9.50 g; 0.138 mole) in water (20 ml) was added dropwise thereto in such manner that the temperature of the reaction mixture did not exceed 10° C. Thereafter, the mixture was stirred for 30 minutes under ice-cooling. After addition of 4.50 g of urea (0.075 mole), the mixture was slowly added dropwise to 300 ml of boiling water and the whole mixture was refluxed for 5 minutes. After cooling, the mixture was stirred under ice-cooling, made alkaline with ammonia water, and extracted with chloroform. The chloroform layer was washed with a saturated aqueous solution of sodium chloride, dried over magnesium sulfate (dehydration) and concentrated under reduced pressure. The residue was converted to the hydrochloride in the conventional manner. Recrystallization from ethanol gave 22.0 g (64%) of the object compound as crystals, m.p. 280°–283° C. (decomposition). The physical characteristics of this compound were in complete agreement with those of the compound obtained in Example 1.

We claim:

1. A pyrrolizidine derivative or a pharmaceutically acceptable salt thereof, said derivative being N-(3'-hydroxy-2',6'-dimethylphenyl)-8-pyrrolizidineacetamide of the formula

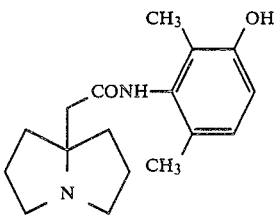

2. A pharmaceutical composition useful for the treatment of arrhythmia, comprised of the pyrrolizidine derivative or pharmaceutically acceptable salt of claim 1 and a pharmaceutically acceptable carrier.

* * * * *